United States Patent
Stauffer et al.

(10) Patent No.: US 8,377,954 B2
(45) Date of Patent: Feb. 19, 2013

(54) BICYCLIC SPIROPIPERIDINE BETA-SECRETASE INHIBITORS FOR THE TREATMENT OF ALZHEIMER'S DISEASE

(75) Inventors: Shaun R. Stauffer, Schwenksville, PA (US); Samuel L. Graham, Schwenksville, PA (US)

(73) Assignee: Merck, Sharp & Dohme, Corp, Rahway, NJ (US)

( * ) Notice: Subject to any disclaimer, the term of this patent is extended or adjusted under 35 U.S.C. 154(b) by 390 days.

(21) Appl. No.: 12/522,056

(22) PCT Filed: Dec. 28, 2007

(86) PCT No.: PCT/US2007/026469
§ 371 (c)(1),
(2), (4) Date: Jul. 2, 2009

(87) PCT Pub. No.: WO2008/085509
PCT Pub. Date: Jul. 17, 2008

(65) Prior Publication Data
US 2010/0076004 A1    Mar. 25, 2010

Related U.S. Application Data

(60) Provisional application No. 60/878,518, filed on Jan. 4, 2007.

(51) Int. Cl.
C07D 401/14 (2006.01)
A61K 31/438 (2006.01)

(52) U.S. Cl. ............................. 514/278; 546/17; 546/20

(58) Field of Classification Search ................... 546/17, 546/20; 514/278
See application file for complete search history.

(56) References Cited

U.S. PATENT DOCUMENTS

| | | |
|---|---|---|
| 4,710,504 A | 12/1987 | Baldwin et al. |
| 7,045,527 B2 | 5/2006 | Chen et al. |
| 7,049,321 B2 | 5/2006 | Fisher et al. |
| 2006/0052406 A1 | 3/2006 | Fisher et al. |
| 2007/0021454 A1 | 1/2007 | Coburn et al. |

FOREIGN PATENT DOCUMENTS

| | | |
|---|---|---|
| WO | 2006044497 A2 | 4/2006 |
| WO | WO2006/058303 | 6/2006 |
| WO | 2006130416 A2 | 7/2006 |
| WO | 2008030412 A2 | 3/2008 |
| WO | 2008045250 A1 | 4/2008 |
| WO | 2008054698 A2 | 5/2008 |

OTHER PUBLICATIONS

Dorwald F. A. Side Reactions in Organic Synthesis, 2005, Wiley: VCH, Weinheim p. IX of Preface.*
Supplementary European Search Report for EP07868113 filed Jan. 4, 2007 mailed on Mar. 7, 2011; 9 pages.

* cited by examiner

*Primary Examiner* — Rita Desai
(74) *Attorney, Agent, or Firm* — Keith D. MacMillan; Gerard M. Devlin

(57) ABSTRACT

The present invention is directed to bicyclic spiropiperidine compounds of formula (I)

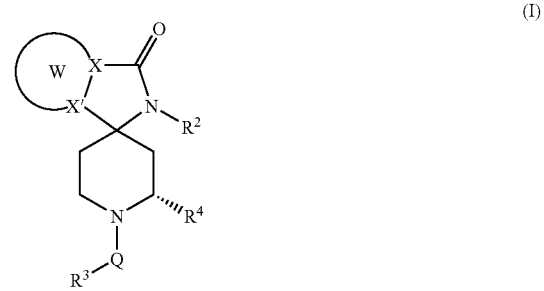

(I)

which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

6 Claims, No Drawings

BICYCLIC SPIROPIPERIDINE BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) of U.S. provisional application Ser. No. 60/878,518, filed Jan. 4, 2007.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to bicyclic spiropiperidine compounds which are useful as inhibitors of the beta secretase enzyme, and are useful in the treatment of diseases in which the beta secretase enzyme is involved, such as Alzheimer's Disease.

BACKGROUND OF THE INVENTION

Alzheimer's Disease is a progressive, neurodegenerative disorder characterized by memory impairment and cognitive dysfunction. Alzheimer's disease is characterized pathologically by the deposition of amyloid in the brain in the form of extra-cellular plaques and intra-cellular neurofibrillary tangles.

The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to bicyclic spiropiperidine compounds of general formula (I)

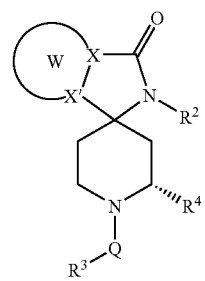

(I)

and pharmaceutically acceptable salts thereof, which are useful as inhibitors of the β-secretase enzyme.

The invention is also directed to pharmaceutical compositions which include a therapeutically effective amount of a compound of formula (I), or pharmaceutically acceptable salts thereof, and a pharmaceutically acceptable carrier. The invention is also directed to methods of treating mammals for diseases in which the β-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to bicyclic spiropiperidine compounds represented by general formula (I)

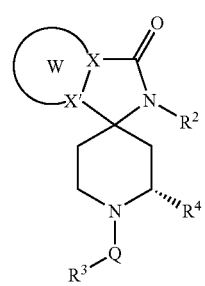

(I)

wherein:

W represents a 5 or 6 membered aromatic or non-aromatic ring cyclic ring fused to the spirocyclic group at the X and X' atoms, wherein one or two of the W carbon ring atoms is optionally replaced by a nitrogen ring atom, and wherein one or two W ring carbon atoms is optionally substituted with a —$C_{1-10}$ alkyl group;

X is selected from the group consisting of
(1) N,
(2) C, or
(3) CH;

X' is selected from the group consisting of
(1) C, or
(2) CH;
$R^2$ is selected from the group consisting of
(1) hydrogen,
(2) —$C_{1-10}$ alkyl,
(3) —$C_{2-10}$ alkenyl,
(4) —$C_{2-10}$ alkynyl,
(5) —$C_{3-12}$ cycloalkyl,
(6) a nonaromatic heterocyclic group having 4 to 8 ring atoms, wherein one ring atom is a heteroatom selected from the group consisting of nitrogen and oxygen,
(7) aryl, and
(8) heteroaryl,
wherein said alkyl, alkenyl, alkynyl, cycloalkyl, heterocyclic group, aryl or heteroaryl $R^2$ moiety is optionally substituted with one or more
(a) halo,
(b) —OH,
(c) —CN,
(d) —$C_{1-10}$ alkyl,
(e) —$C_{3-12}$ cycloalkyl,
(f) —O—$C_{1-10}$ alkyl,
(g) —$C_{0-6}$ alkyl-aryl,
(h) —$C_{0-6}$ alkyl-heteroaryl,
(i) —NC(=O)—$NR^{6A}R^{6B}$,
(j) —NC(=O)—$C_{1-3}$ alkyl-$NR^{6A}R^{6B}$,
(k) —NC(=O)$R^{6A}$,
(l) —$NR^{6A}R^{6B}$, and
(m) a nonaromatic heterocyclic group having 4 to 8 ring atoms, wherein one ring atom is a heteroatom selected from the group consisting of nitrogen and oxygen,
and said alkyl, cycloalkyl, aryl, heteroaryl and heterocyclic moiety is optionally substituted with one or more
(i) halo,
(ii) -OH,
(iii) —CN,
(iv) —$C_{1-6}$ alkyl, wherein said alkyl is optionally substituted with one or more halo,
(v) —$OC_{1-6}$ alkyl,
(vi) —$C_{2-6}$ alkenyl,
(vii) —$SO_2C_{1-3}$ alkyl,
(viii) —$SO_2 NR^{6C}R^{6D}$,
(ix) —$NR^{6C}SO_2C_{1-3}$alkyl,
(x) —$CO_2R^{6C}$, and
(xi) —$CONR^{6C}R^{6D}$;
Q is a bond or $C_{1-6}$ alkyl, wherein said alkyl is optionally substituted with one or more
(a) halo,
(b) —OH,
(c) —CN,
(d) —$C_{1-10}$ alkyl,
(e) —$C_{3-12}$ cycloalkyl,
(f) —O—$C_{1-10}$ alkyl,
(g) aryl, and
(h) heteroaryl;
$R^3$ is selected from the group consisting of
(1) hydrogen,
(2) —$C_{1-10}$ alkyl,
(3) —$C_{2-10}$ alkenyl,
(4) —$C_{2-10}$ alkynyl,
(5) —$C_{3-12}$ cycloalkyl,
(6) —$C_{3-12}$ cycloalkenyl,
(7) aryl, and
(8) heteroaryl,
wherein said alkyl, alkenyl, alkynyl, cycloalkyl, cycloalkenyl, aryl or heteroaryl $R^3$ moiety is optionally substituted with one or more
(a) halo,
(b) —OH,
(c) —CN,
(d) —$C_{1-10}$ alkyl,
(e) —$C_{2-10}$ alkenyl,
(f) —$C_{3-12}$ cycloalkyl,
(g) —O—$C_{3-12}$ cycloalkyl,
(h) —O—$C_{1-10}$ alkyl,
(i) —O—$C_{3-12}$ nonaromatic heterocyclic, wherein said heterocyclic group has from 4 to 8 ring atoms, wherein one ring atom is a heteroatom selected from the group consisting of nitrogen and oxygen,
(j) aryl,
(k) heteroaryl,
(l) —$NR^{6A}R^{6B}$,
and said alkyl, alkenyl, cycloalkyl, aryl and heteroaryl moiety is optionally substituted with one or more
(i) halo,
(ii) -OH,
(iii) —CN,
(iv) —$C_{1-6}$ alkyl, wherein said alkyl is optionally substituted with one or more halo,
(v) —$OC_{1-6}$ alkyl,
(vi) —$NR^{6C}R^{6D}$,
(vii) —$C_{2-6}$ alkenyl,
(viii) —$SO_2C_{1-3}$ alkyl,
(ix) —$SO_2 NR^{6C}R^{6D}$, or
(x) —$CONR^{6C}R^{6D}$,
provided that when Q is a bond then $R^3$ must be hydrogen;
$R^4$ is selected from the group consisting of
(1) hydrogen,
(2) —$C_{1-10}$ alkyl,
(3) —$C_{3-4}$ alkenyl, and
(4) aryl,
wherein said alkyl, alkenyl or aryl $R^4$ group is optionally substituted with one or more
(a) halo,
(b) —OH
(c) —$C_{1-6}$ alkyl,
(d) —CN,
(e) —O—$C_{1-10}$ alkyl,
(f) —$NR^8R^9$, wherein $R^8$ and $R^9$ are selected from the group consisting of
(i) hydrogen, and
(ii) —$C_{1-6}$ alkyl,
(g) —$S(O)_m$—$C_{1-6}$ alkyl, wherein m is 0, 1 or 2,
(h) —C(=O)—$R^7$, wherein $R^7$ is selected from the group consisting of
(i) hydrogen,
(ii) OH,
(iii) —$C_{1-6}$ alkyl,
(iv) —$OC_{1-6}$ alkyl, and
(v) aryl;
$R^{6A}$, $R^{6B}$, $R^{6C}$ and $R^{6D}$ are selected from the group consisting of
(1) hydrogen,
(2) —$C_{1-6}$ alkyl,
(3) —$C_{3-7}$ cycloalkyl,
(4) —$C_{0-6}$ alkyl-aryl,
(5) —$CO_6$alkyl-heteroaryl,
(6) halo, and
(7) a nonaromatic heterocyclic group having 4 to 8 ring atoms, wherein one ring atom is a heteroatom selected from the group consisting of nitrogen and oxygen, wherein said alkyl, cycloalkyl, aryl or heteroaryl $R^{6A}$ or $R^{6B}$ moiety is optionally substituted with one or more
(a) halo,
(b) —$C_{1-6}$ alkyl,
(c) —O—$C_{1-6}$ alkyl, and
(d) —$NO_2$;
and pharmaceutically acceptable salts thereof.

In one embodiment of the compounds of formula (I), W represents a 5 or 6-membered aromatic ring.

In another embodiment of the compounds of formula (IA), W represents a 5 or 6-membered non-aromatic ring.

In one embodiment of compounds of formula (I), Q is $CH_2$ and $R^3$ is optionally substituted phenyl. Suitable substituents for the phenyl group are halo, —OH, —CN, —$C_{1-10}$ alkyl or —O—$C_{1-10}$ alkyl.

In one embodiment of compounds of formula (I), $R^2$ is optionally substituted phenyl. Suitable substituents for the phenyl group are halo, —OH, —CN, —$C_{1-10}$ alkyl or —O—$C_{1-10}$ alkyl.

In one embodiment of the compounds of formula (I), the compounds are compounds of formula (IA)

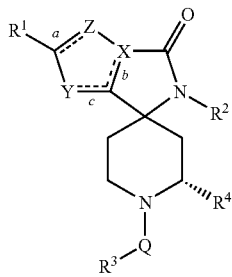

(IA)

wherein:
bonds a, b and c are each selected from either a single or double bond, provided that both b and c cannot be double bonds;
Z is selected from the group consisting of
(1) —CH—,
(2) —$CH_2$—,
(3) —CH=CH—,
(4) —$CHCH_2$—, or
(5) —$CH_2CH_2$—,
provided that when a is a double bond then Z is —CH— or —$CHCH_2$—, and when a is a single bond then Z is —$CH_2$—, —CH=CH—, or —$CH_2CH_2$—;
Y is selected from the group consisting of
(1) N,
(2) NH,
(3) $CR^{5A}$ and
(4) $CR^{5A}R^{5B}$,
provided that when c is a double bond then Y is $CR^{5A}$ or N, and when c is a single bond then Y is NH or $CR^{5A}R^{5B}$;
wherein $R^{5A}$ and $R^{5B}$ are selected from the group consisting of
(a) hydrogen,
(b) —$C_{1-10}$ alkyl,
(c) —$C_{2-10}$ alkenyl,
(d) —$C_{3-12}$ cycloalkyl,
(e) —$C_{0-6}$ alkyl-aryl, and
(f) —$C_{0-6}$ alkyl-heteroaryl,
and further provided that at least one of X or Y is N or NH;

$R^1$ is selected from the group consisting of
(1) hydrogen, and
(2) —$C_{1-10}$ alkyl;
and Q, $R^2$, $R^3$ and $R^4$ are as defined for formula (I);
and pharmaceutically acceptable salts thereof.

In one embodiment of the compounds of formula (IA), a and c are single bonds, and b is a double bond. In one embodiment, a and c are single bonds, b is a double bond, X is C, Y is NH and Z is $CH_2CH_2$.

In another embodiment of the compounds of formula (IA), a and b are double bonds, and c is a single bond. In another embodiment, a and b are double bonds, c is a single bond, X is C, Y is NH and Z is $CH_2$.

In another embodiment of the compounds of formula (IA), a and c are double bonds and b is a single bond. In another embodiment, a and c are double bonds, b is a single bond, X and Y are N and Z is CH.

In another embodiment of the compounds of formula (IA), $R^1$ is hydrogen or $C_{1-4}$ alkyl (for example, $R^1$ is methyl).

In another embodiment of compounds of formula (IA), Q is $CH_2$ and $R^3$ is optionally substituted phenyl. Suitable substituents for the phenyl group are halo, —OH, —CN, —$C_{1-10}$ alkyl or —O—$C_{1-10}$ alkyl.

In another embodiment of compounds of formula (IA), $R^2$ is optionally substituted phenyl. Suitable substituents for the phenyl group are halo, —OH, —CN, —$C_{1-10}$ alkyl or —O—$C_{1-10}$ alkyl.

In particular embodiments, the invention is directed to compounds of the invention of Examples 1-10, as follows:
1-Benzyl-6'-(3-fluorophenyl)-1',2',3',4'-tetrahydrospiro[piperidine-4,7'-pyrrolo[3,4-b]pyridin]-5'(6'H)-one;
trans-5R,7S-1-Benzyl-6'-(3-fluorophenyl)-2-methyl-1',2',3',4'-tetrahydrospiro[piperidine-4,7'-pyrrolo[3,4-b]pyridin]-5'(6'H)-one;
1-Benzyl-5'-(3-fluorophenyl)-1'H-spiro[piperidine-4,6'-pyrrolo[3,4-b]pyrrol]-4'(5'H)-one;
trans-5R,7S-6-(3-fluorophenyl)-1'-(3-isopropoxybenzyl)-2-isopropyl-2'-methylspiro[imidazo[1,5-a]imidazole-7,4'-piperidin]-5(6H)-one;
1'-Benzyl-6-[4-fluoro-4'-(methylsulfonyl)biphenyl-2-yl]-2'-methylspiro[imidazo[1,5-a]imidazole-7,4'-piperidin]-5(6H)-one;
trans-(5R,7S)-1'-benzyl-6-(3-fluorophenyl)-2-isopropyl-2'-methylspiro[imidazo[1,5-a]imidazole-7,4'-piperidin]-5(6H)-one;
trans-(5R,7S)-6-(3-fluorophenyl)-1'-(3-isopropoxybenzyl)-2'-methylspiro[imidazo[1,5-a]imidazole-7,4'-piperidin]-5(6H)-one;
trans-(5R,7S)-2-ethyl-6-(3-fluorophenyl)-1'-(3-isopropoxybenzyl)-2'-methylspiro[imidazo[1,5-a]imidazole-7,4'-piperidin]-5(6H)-one;
trans-(5R,7S)-2-tert-butyl-6-(3-fluorophenyl)-1'-(3-isopropoxybenzyl)-2'-methylspiro[imidazo[1,5-a]imidazole-7,4'-piperidin]-5(6H)-one; and
1'-(cyclobutylmethyl)-6-[4-fluoro-4'-(methylsulfonyl)biphenyl-2-yl]spiro[imidazo[1,5-a]imidazole-7,4'-piperidin]-5(6H)-one;
and pharmaceutically acceptable salts thereof.

The invention is also directed to methods of treating mammals for diseases in which the β-secretase enzyme is involved, such as Alzheimer's disease, by administering a therapeutically effective amount of a compound of any of the embodiments of formula (I) and (IA).

The invention is also directed to pharmaceutical compositions which include an effective amount of a compound of any of the embodiments of formula (I) and (IA) or pharmaceutically acceptable salts thereof, and a pharmaceutically acceptable carrier.

The invention is further directed to a method for the manufacture of a medicament or a composition for inhibiting β-secretase enzyme activity in humans and animals comprising combining a compound of any of the embodiments of formula (I) and (IA) or a pharmaceutically acceptable salt thereof, with a pharmaceutical carrier or diluent.

In one embodiment, the invention is directed to methods of inhibiting BACE1 enzyme activity, by administering a therapeutically effective amount of a compound of any of the embodiments of formula (I) and (IA).

In another embodiment, the invention is directed to methods of inhibiting BACE2 enzyme activity, by administering a therapeutically effective amount of a compound of any of the embodiments of formula (I) and (IA).

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Suitable alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

The term "$C_0$ alkyl," for example in the term "—$C_0$alkyl-$C_{6-12}$ aryl", refers to a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Suitable alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Suitable alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, as well as bridged and fused ring carbocycles, such as spiro fused ring systems.

Suitable cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

As used herein, the term "cycloalkenyl," by itself or as part of another substituent, means a cyclic hydrocarbon radical having a single C—C double bond, and the number of carbon atoms designated (e.g., $C_{3-12}$ cycloalkenyl means a cycloalkenyl group having from three to twelve carbon atoms). The term cycloalkenyl as used herein includes mono-, bi- and tricyclic saturated carbocycles, as well as bridged and fused ring carbocycles, such as spiro fused ring systems. Suitable cycloalkenyl groups for use in the invention are monocyclic $C_{3-8}$ cycloalkenyl groups, having from three to eight carbon atoms. Exemplary monocyclic cycloalkenyl groups include cyclopropenyl, cyclobutenyl, cyclopentenyl, cyclohexenyl and the like.

As used herein, the term "heterocyclic," by itself or as part of another substituent, means a cycloalkyl group as defined above, in which one or more of the ring carbon atoms is replaced with a heteroatom (such as N or O). Suitable non-aromatic heterocyclic groups for use in the invention include piperidinyl, piperazinyl, morpholinyl, tetrahydropyranyl, tetrahydrofuranyl, pyrrolidinyl, pyrazolidinyl and imidazolidinyl. In certain embodiments, heterocyclic groups for use in the invention have four to eight ring atoms and a single nitrogen or oxygen heteroatom.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems (such as fused ring systems) as well as single ring systems, and includes multiple ring systems wherein part of the molecule is aromatic and part is non-aromatic. A suitable single ring aryl group for use in the invention is phenyl. Suitable fused ring aryl groups include naphthyl, tetrahydronaphthyl and indanyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems. Exemplary heteroaryl groups have from 5 to 12 ring atoms. In particular embodiments, the heteroaryl groups useful in the invention have 5 or 6 ring atoms. Exemplary heteroaryl groups include pyrazinyl, pyrazolyl, pyridazinyl, pyridyl, pyrimidinyl, pyrrolyl, tetrazolyl, furanyl, imidazolyl, indazolyl, triazinyl, pyranyl, thiazolyl, thienyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment.

As used herein, the term "beta-secretase" or "β-secretase" refers to an enzyme that is sometimes known in the literature as "BACE", "BACE1" (see, e.g., Vassar et al., 1999, *Science* 286:735-741), or "BACE2" (see, e.g., Farzan et al., 2000, *PNAS* 97:9712-9717). BACE1 is a 501 amino acid membrane-bound aspartic protease. BACE1 has all the known functional properties and characteristics of β-secretase. BACE2, also called Asp-1 or memapsin-1, is a second member of the BACE family of membrane-bound aspartic proteases. See Roggo, *Current Topics in Medicinal Chemistry*, 2002, 2:359-370, for a further discussion of the differences between BACE1 and BACE2.

The compounds of the invention are inhibitors of both the BACE1 and BACE2 enzyme.

The compounds of the invention have at least one asymmetric center. Additional asymmetric centers may be present depending upon the nature of the various substituents on the molecule.

Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formula (I) and (IA).

Compounds described herein may contain one or more double bonds, and may thus give rise to cis/trans isomers as well as other configurational isomers. The present invention includes all such possible isomers as well as mixtures of such isomers.

Formula (I) and (IA) are shown above without a definite stereochemistry at certain positions. The present invention includes all stereoisomers of formulas (I) and (IA) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

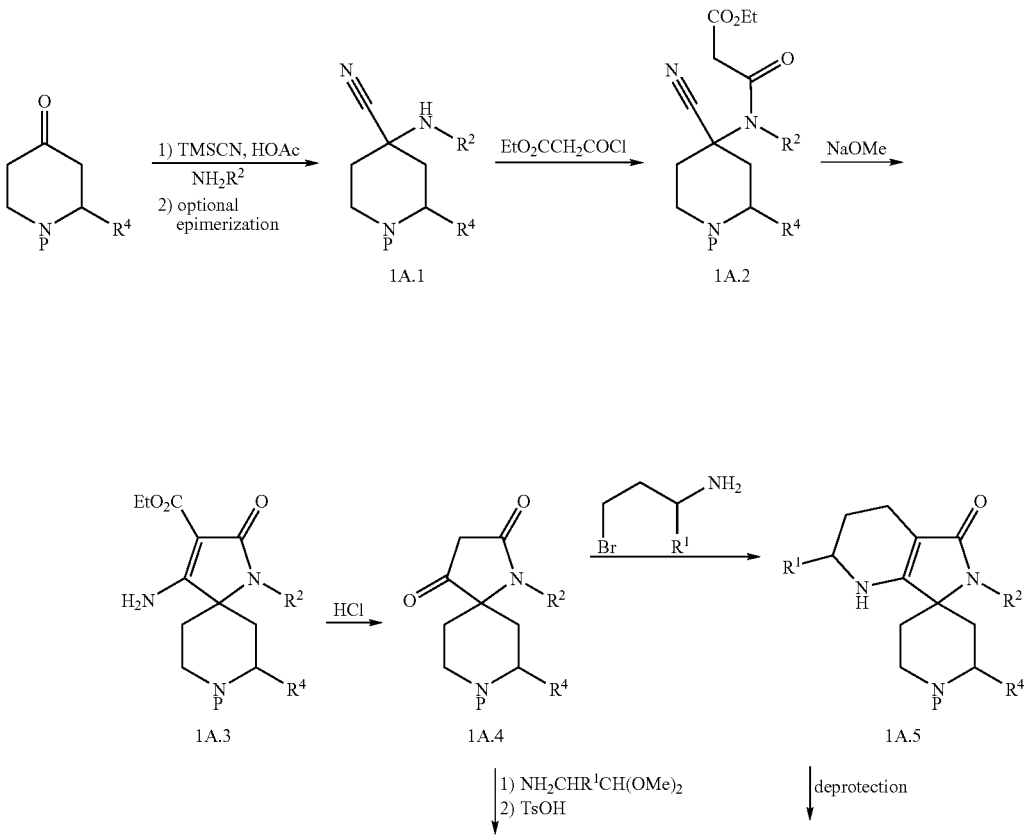

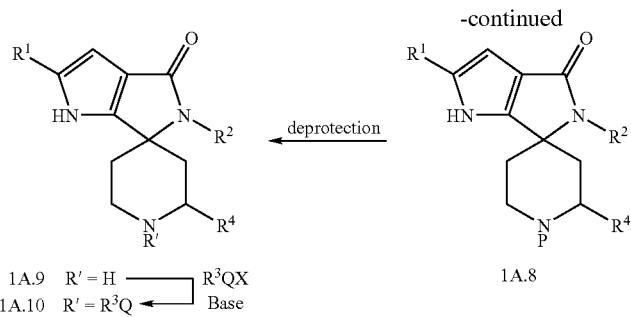
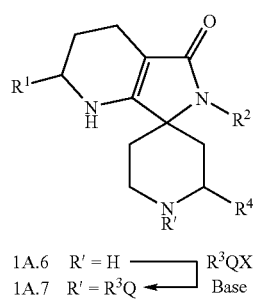

1A.9  R' = H  ⟶ R³QX
1A.10 R' = R³Q ⟵ Base 1A.8

1A.6  R' = H  ⟶ R³QX
1A.7 R' = R³Q ⟵ Base

Examples of types 1A.5-1A.10 are illustrated in Scheme 1A. Beginning with a suitable N-protected piperidinone, Strecker reaction with various amines gives adducts of type 1A.1. Reaction with malonyl chloride, followed by based mediated cyclization to give 1A.3 and decarboxylation with HCl gives key intermediate of type 1A.4. Intermediates of type 1A.4 can be further reacted with an appropriate bromoaminopropane to give examples (P=Bn) or intermediates of type 1A.5 (P=Bn). 1A.5 can be deprotected to give intermediates of type 1A.6 (R'=H). Alternatively 1A.6 can be alkylated to give examples 1A.7. Alternatively 1A.4 can be reacted with an aminoacetal and then treated with tosic acid to give examples (P=Bn) or intermediates of type 1A.8. 1A.8 can be deprotected to give intermediates 1A.9 and subsequently alkylated with alternate R³Q groups to give examples of type 1A.10.

Scheme 1B

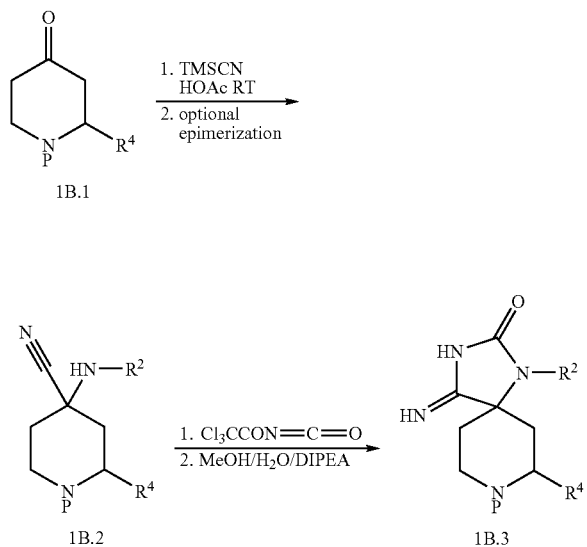

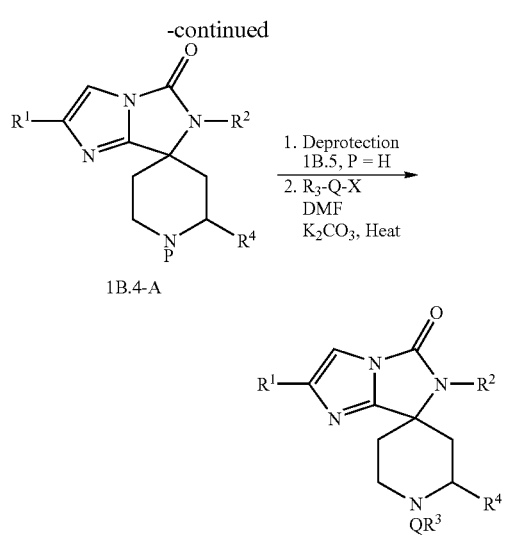

Method A

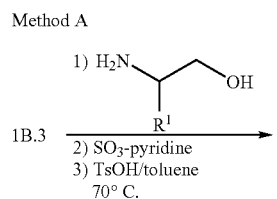

Method B

Method C

Scheme 1B depicts general methods utilized to prepare examples of type 1B.6. One of three methods may be utilized beginning from intermediate 1B.3 (described in International Patent Application WO 2007/11833). Method A involves treatment with a 1,2-aminoalcohol followed by oxidation and cyclization to give 1B.4-A. 1B.4-A can be deprotected to give intermediate 1B.5 and alkylated to give examples of type 1B.6. Method B is similar to A but involves the use of an aminoacetal in the displacement step which readily cyclizes to give 1B.4-B, which are structurally similar to 1B.4-A. Manipulation as before gives final examples of type 1B.6. Method C utilizes 1B.3 in an alkylation reaction using various alpha-bromoketones to give intermediates 1B.4-C which are

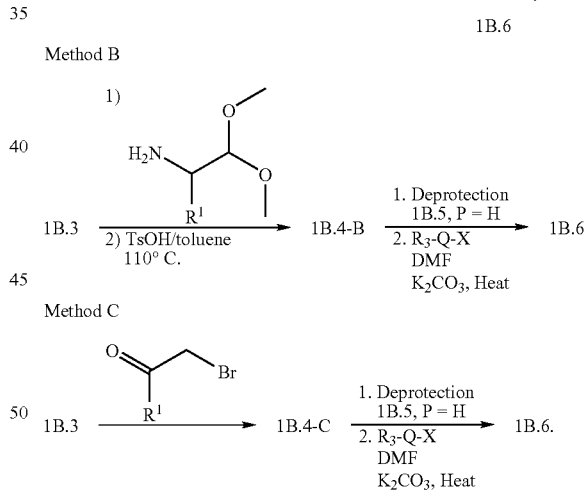

structurally also represented by 1B.4-A. Similar manipulations from 1B.4-C gives examples 1B.5 and 1B.6

Scheme 1C

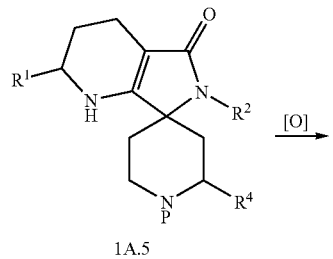

1A.5

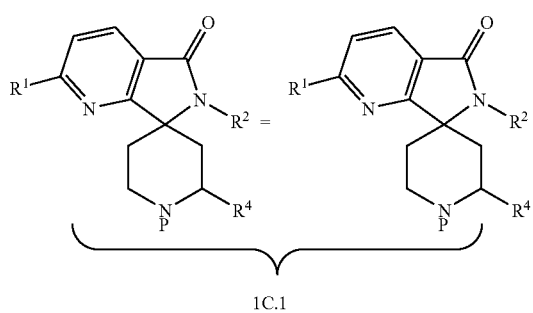

1C.1

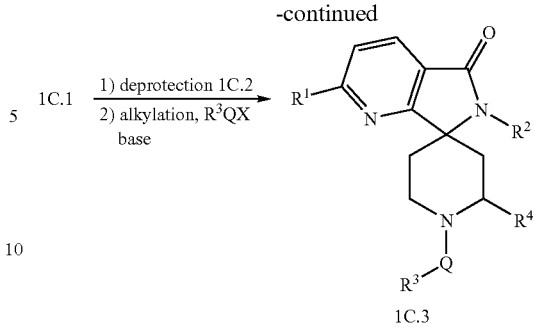

1C.3

Scheme 1C depicts the synthesis of examples of type 1C.3. Starting from intermediates of type 1A.5 (Scheme 1A) oxidation using DDQ or equivalent oxidants, gives intermediate bicyclic pyridines of types 1C.1. Deprotection gives 1C.2 and final alkylation as before gives 1C.3

Scheme 2A describes the synthesis of ortho biphenyl examples of type 2A.3, 2A.4 and 2A.5. One of three methods, which vary on the entry point of the desired biphenyl, may be used to prepare analogs within this structural type. Method A starting from 1-benzyl-2-methylpiperidin-4-one (preparation described by M.-J. Blanco-Pilado et al in International Patent Application WO2004/094380) involves first a Strecker with an o-haloaniline to give 2A.1-A followed by a Suzuki coupling and ring closure with to give 2A.3. The benzyl can be removed with Pd/C and $H_2$ to give 2A.4. Further elaboration via alkylation gives examples of type 2A.5. Method B uses o-biphenylanilines initially in a Strecker reaction to give 2A.2-B followed by ring-closure and functional group manipulation as before. Method C starts from 2A.1-A and begins with ring-closure, then piperidine modification as desired and final Suzuki coupling to give additional examples of type 2A.5

Scheme 2A

Method A

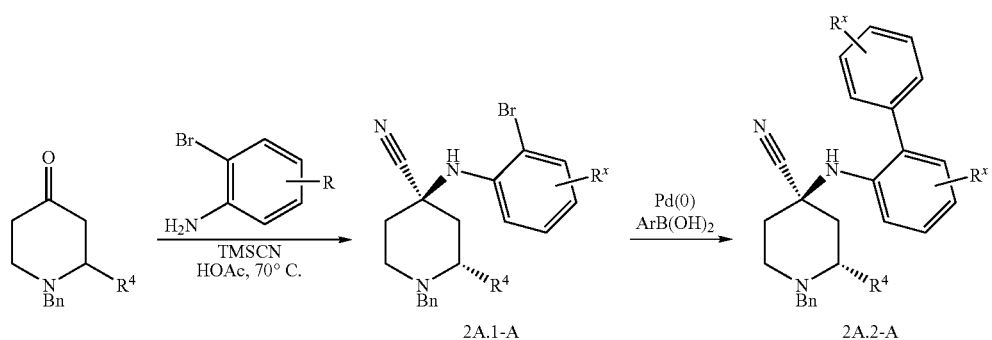

Method B

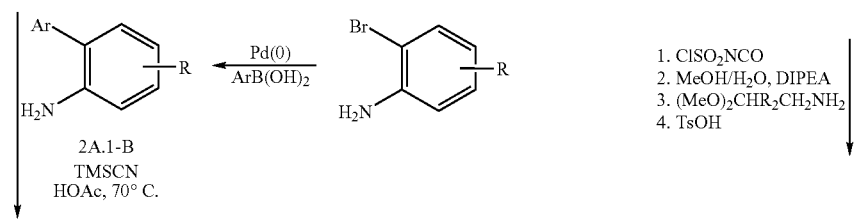

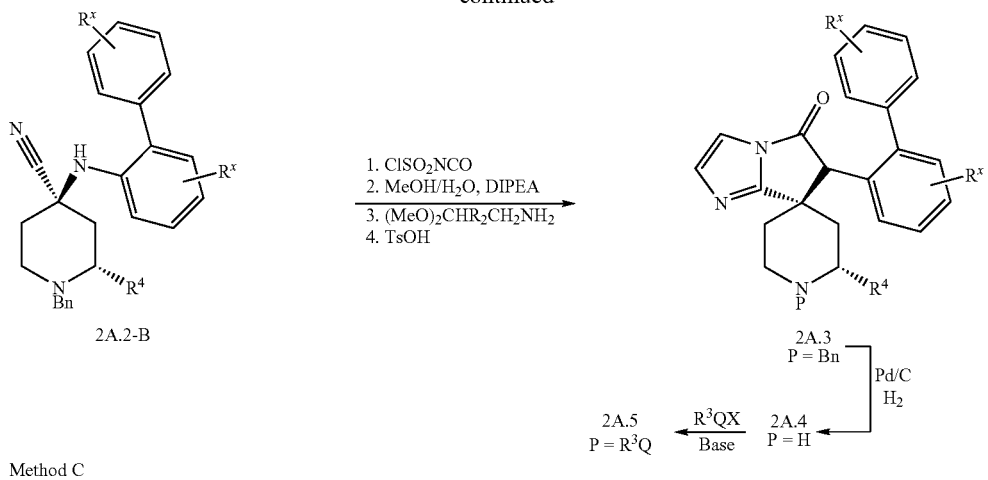

Method C

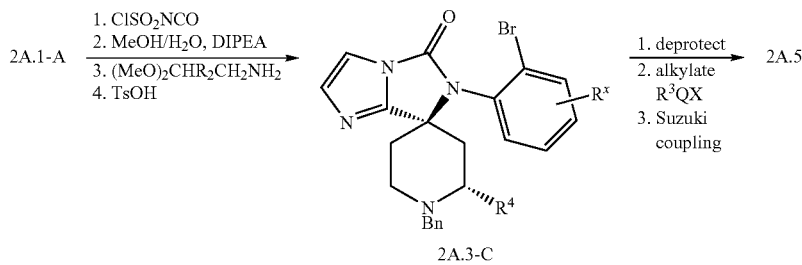

The term "substantially pure" means that the isolated material is at least 90% pure, as assayed by analytical techniques known in the art. In one embodiment, the isolated material is at least 95% pure. In another embodiment, the isolated material is at least 99% pure.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

The present invention is directed to the use of the compounds of formula (I) or (IA) disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors or gamma-secretase inhibitors; glycine transport inhibitors, tau phosphorylation inhibitors; blockers of Aβ oligomer formation; p25/CDK5 inhibitors; HMG-CoA reductase inhibitors; PPAR gamma agonists, such as pioglitazone and rosiglitazone; NK1/NK3 receptor antagonists; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; NR2B antagonists; androgen receptor modulators; acetylcholinesterase inhibitors such as galantamine, rivastigmine, donepezil, and tacrine; mGluR5 modulators; growth hormone secretagogues such as ibutamoren, ibutamoren mesylate, and capromorelin; histamine $H_3$ antagonists; AMPA agonists; PDE IV inhibitors; $GABA_A$ inverse agonists; $GABA_A\alpha5$ receptor ligands; $GABA_B$ receptor ligands; potassium channel blockers; neuronal nicotinic agonists; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In the pharmaceutical composition the active compound, which is a compound of the invention, is included in an amount sufficient to produce the desired effect upon the process or condition of diseases. Accordingly, the pharmaceutical compositions of the present invention encompass any composition made by admixing a compound of the invention and a pharmaceutically acceptable carrier.

The carrier may take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain a compound of the invention in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a composition of this invention may be prepared by compression or molding, optionally with one or more accessory ingredients or adjuvants. Compressed tablets may be prepared by compressing, in a suitable machine, a compound of the invention in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. In certain embodiments, each tablet contains from about 0.1 mg to about 500 mg of the active ingredient and each cachet or capsule contains from about 0.1 mg to about 500 mg of the compound of the invention.

Compositions for oral use may also be presented as hard gelatin capsules wherein the compound of the invention is mixed with an inert solid diluent, for example, calcium carbonate, calcium phosphate or kaolin, or as soft gelatin capsules wherein the compound of the invention is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the compound of the invention in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of the invention, to produce a cream or ointment having a desired consistency.

Pharmaceutical compositions of this invention can also be in a form suitable for rectal administration wherein the carrier is a solid. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the invention are indicated, generally satisfactory results are obtained when the compounds of the invention are administered at a daily dosage of from about 0.1 mg to about 100 mg per kg of animal body weight. For example, the compounds may be given as a single daily dose or in divided doses two to six times a day, or in sustained release form. The total daily dosage is from about 1.0 mg to about 2000 mg (for example, from about 0.1 mg to about 20 mg per kg of body weight). In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, for example once or twice per day.

The amount of the compound of the invention that may be combined with the carrier materials to produce a single dosage form will vary depending upon the host treated and the particular mode of administration. For example, a formulation intended for the oral administration to humans may conveniently contain from about 0.005 mg to about 2.5 g of a compound of the invention, compounded with an appropriate and convenient amount of carrier material. Unit dosage forms will generally contain between from about 0.005 mg to about 1000 mg of the compound of the invention, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is performed using a biotinylated BACE substrate. The Km of the substrate is greater than 100

μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared starting from 100 μM with three fold series dilution. Solutions of the inhibitor in DMSO are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 200 μM. Such a result is indicative of the intrinsic activity of the compounds in use as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

INTERMEDIATE 1A.1-1

1-Benzyl-4-[(3-fluorophenyl)amino]piperidine-4-carbonitrile

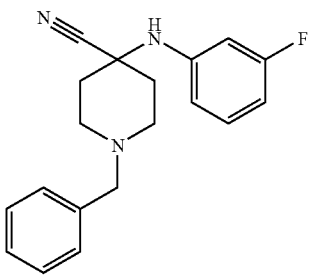 [SMILES: N#CC1(Nc2cccc(F)c2)CCN(Cc2ccccc2)CC1]

To a solution of 1-benzyl-4-piperidinone (25.0 g, 132 mmol) in acetic acid (132 ml) at 0° C. were added 3-fluoroaniline (12.7 ml, 132 mmol) and trimethylsilyl cyanide (17.6 ml, 132 mmol) dropwise. The reaction was allowed to warm to rt and stir for 18 h. The reaction was poured onto a mixture of ice (200 g) and ammonium hydroxide (200 ml), and the product was extracted with dichloromethane (4×500 ml). The combined organic extractions were washed with brine, dried over sodium sulfate, filtered, and concentrated in vacuo to give a brown solid. The crude material was recrystallized from diethyl ether to afford 1-benzyl-4-[(3-fluorophenyl)amino]piperidine-4-carbonitrile as a beige solid (67%). LCMS. (M+H) 310.1. $^1$H NMR (400 MHz, DMSO) δ 7.33 (m, 4H), 7.25 (m, 1H), 7.19 (q, J=7.8 Hz, 1H), 6.66 (dd, J=8.2, 2.0 Hz, 1H), 6.59 (dt, J=12.2, 2.2 Hz, 1H), 6.50 (td, J=8.5, 2.2 Hz, 1H), 6.42 (s, 1H), 3.52 (s, 2H), 2.76 (d, J=11.2 Hz, 2H), 2.30 (t, J=10.9 Hz, 4H), 1.82 (t, J=10.5 Hz, 2H).

INTERMEDIATE 1A.2-1

Ethyl 3-[(1-benzyl-4-cyanopiperidin-4-yl)(3-fluorophenyl)amino]-3-oxopropanoate

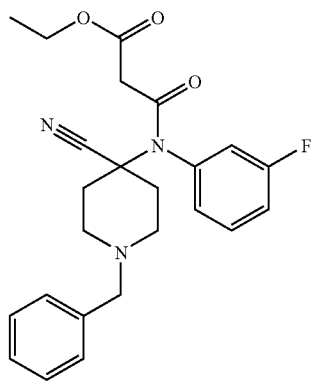 [SMILES: CCOC(=O)CC(=O)N(c1cccc(F)c1)C1(C#N)CCN(Cc2ccccc2)CC1]

To a solution of 1-benzyl-4-[(3-fluorophenyl)amino]piperidine-4-carbonitrile (Intermediate 1A.1-1, 9.0 g, 29.1 mmol) in dichloromethane (150 ml) were added ethyl malonyl chloride (4.9 ml, 37.8 mmol) and 2,6-lutidine (5.1 ml, 43.6 mmol). The reaction was allowed to stir at rt for 2.5 h. Additional ethyl malonyl chloride (1.1 ml, 8.7 mmol) was added, and the reaction was allowed to stir for 30 min. The reaction was diluted with dichloromethane and washed with water and brine. The organic portion was dried over sodium sulfate, filtered, and concentrated in vacuo to yield a 1:1 mixture of desired ester ethyl 3-[(1-benzyl-4-cyanopiperidin-4-yl)(3-fluorophenyl)amino]-3-oxopropanoate and its acid 3-[(1-benzyl-4-cyanopiperidin-4-yl)(3-fluorophenyl)amino]-3-oxopropanoic acid (quant).

INTERMEDIATE 1A.3-1

Ethyl-4-amino-8-benzyl-1-(3-fluorophenyl)-2-oxo-1,8-diazaspiro[4.5]dec-3-ene-3-carboxylate

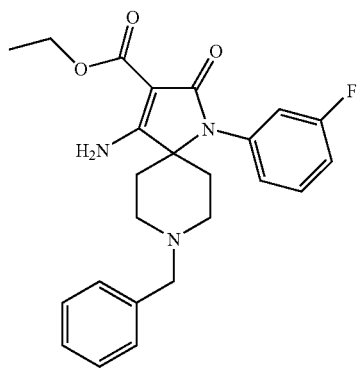 [SMILES: CCOC(=O)C1=C(N)C2(CCN(Cc3ccccc3)CC2)N(c2cccc(F)c2)C1=O]

To a solution of ester ethyl 3-[(1-benzyl-4-cyanopiperidin-4-yl)(3-fluorophenyl)amino]-3-oxopropanoate (and its acid 3-[(1-benzyl-4-cyanopiperidin-4-yl)(3-fluorophenyl)amino]-3-oxopropanoic acid) (Intermediate 1A.2-1, 14.9 g, 35.2 mmol) in methanol (20 ml) was added sodium methoxide (2.3 g, 42.2 mmol). The reaction was allowed to stir at rt for 1 h. The reaction was concentrated to yield a mixture (2.5:1) of ethyl and methyl 4-amino-8-benzyl-1-(3-fluorophenyl)-2-oxo-1,8-diazaspiro[4.5]dec-3-ene-3-carboxylate (96%). LCMS (M+H) 424.1.

INTERMEDIATE 1A.4-1

8-Benzyl-1-(3-fluorophenyl)-1,8-diazaspiro[4.5]decane-2,4-dione

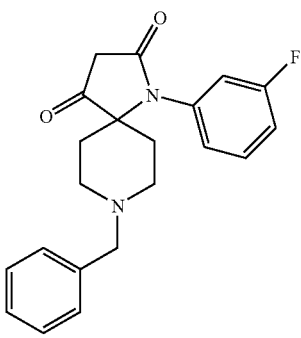 [SMILES: O=C1CC(=O)C2(CCN(Cc3ccccc3)CC2)N1c1cccc(F)c1]

A mixture of ethyl and methyl 4-amino-8-benzyl-1-(3-fluorophenyl)-2-oxo-1,8-diazaspiro[4.5]dec-3-ene-3-carboxylate (Intermediate 1A.3-1, 14.3 g, 33.7 mmol) in 6N HCl was fitted with a reflux condenser and allowed to stir at 80° C. for 18 h. The reaction was cooled to 0° C. and adjusted to pH 10 with the addition of conc aq NaOH. The aqueous solution was extracted repeatedly with EtOAc. The combined organic extractions were dried over sodium sulfate, filtered, and concentrated to yield the crude product as a red foam. The material was recrystallized from dichloromethane to afford 8-benzyl-1-(3-fluorophenyl)-1,8-diazaspiro[4.5]decane-2,4-dione as a pink solid (49%). LCMS (M+H) 353.1. $^1$H NMR (400 MHz, CD$_3$OD) δ 7.40 (s, 5H), 7.26 (s, 2H), 7.10 (m, 1H), 6.97 (m, 2H), 4.09 (s, 2H), 3.72 (s, 2H), 3.10 (s, 2H), 2.70 (m, 1.5H), 2.05 (m, 4.5H).

INTERMEDIATE 1A.1-2 trans-1-benzyl-4-[(3-fluorophenyl)amino]-2-methylpiperidine-4-carbonitrile

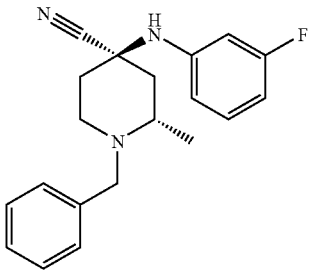 [SMILES: C[C@H]1C[C@](C#N)(Nc2cccc(F)c2)CCN1Cc1ccccc1]

To a solution of 1-benzyl-2-methylpiperidin-4-one (preparation similar to that described by M.-J. Blanco-Pilado et al. in International Patent Application WO2004/094380 using benzylamine as the amine, 40.0 g, 197 mmol) in acetic acid (200 ml) at 0° C. were added 3-fluoroaniline (18.9 ml, 197 mmol) and trimethylsilyl cyanide (26.2 ml, 197 mmol) dropwise. The reaction was allowed to warm to rt and stirred for 18 h. The reaction was then heated to 70° C. for 24 h to affect epimerization of the cis isomer to the desired trans isomer. The reaction was neutralized with a mixture of ice and ammonium hydroxide, and the product was extracted with dichloromethane (2×). The combined organic extractions were dried over sodium sulfate, filtered, and concentrated in vacuo to afford the crude product as a viscous red oil with significant impurity. A portion of the crude material was recrystallized from cold ethanol and purified via flash chromatography (silica, 20% EtOAc/hexanes with 1% diisopropylethylamine) to afford trans-1-benzyl-4-[(3-fluorophenyl)amino]-2-methylpiperidine-4-carbonitrile (13%). LCMS (M+H) 324.1. $^1$H NMR (400 MHz, CD$_3$OD) δ 7.34-7.21 (m, 5H), 7.15 (q, J=7.8 Hz, 1H), 6.65 (dd, J=8.2, 2.2 Hz, 1H), 6.56 (dt, J=11.8, 2.2 Hz, 1H), 6.47 (td, J=8.5, 2.3 Hz, 1H), 4.11 (d, J=13.2 Hz, 1H), 3.16 (d, J=13.2 Hz, 1H), 2.65 (m, 2H), 2.33 (m, 3H), 1.98 (m, 2H), 1.25 (d, J=6.2 Hz, 3H).

INTERMEDIATE 1A.2-2

Ethyl 3-[(trans-1-benzyl-4-cyano-2-methylpiperidin-4-yl)(3-fluorophenyl)amino]-3-oxopropanoate

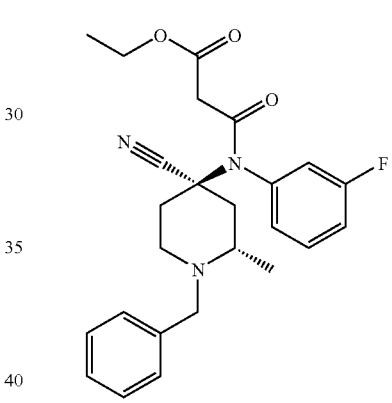

Ethyl 3-[(trans-1-benzyl-4-cyano-2-methylpiperidin-4-yl)(3-fluorophenyl)amino]-3-oxopropanoate was prepared from trans-1-benzyl-4-[(3-fluorophenyl)amino]-2-methylpiperidine-4-carbonitrile (Intermediate 1A.1-2, 1.6 g, 4.9 mmol) and ethyl malonyl chloride (0.8 ml, 5.9 mmol) in a manner similar to Intermediate 1A.2-1. LCMS (M+H) 438.3.

INTERMEDIATE 1A.3-2

Ethyl trans-4-amino-8-benzyl-1-(3-fluorophenyl)-7-methyl-2-oxo-1,8-diazaspiro[4.5]dec-3-ene-3-carboxylate

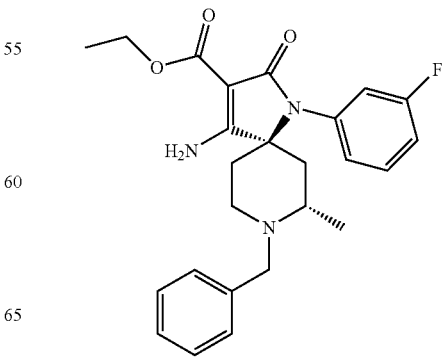

Ethyl trans-4-amino-8-benzyl-1-(3-fluorophenyl)-7-methyl-2-oxo-1,8-diazaspiro[4.5]dec-3-ene-3-carboxylate was prepared from ethyl 3-[(trans-1-benzyl-4-cyano-2-methylpiperidin-4-yl)(3-fluorophenyl)amino]-3-oxopropanoate (Intermediate 1A.2-2, 1.8 g, 4.1 mmol) in a manner similar to Intermediate 1A.3-1. LCMS (M+H) 438.1.

INTERMEDIATE 1A.4-2 trans-8-Benzyl-1-(3-fluorophenyl)-7-methyl-1,8-diazaspiro[4.5]decane-2,4-dione

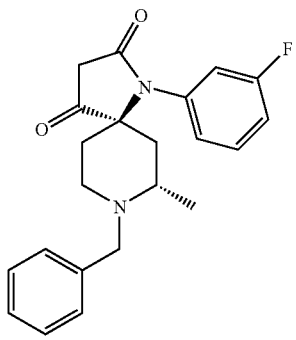 [SMILES: C[C@H]1C[C@]2(CCN1Cc1ccccc1)C(=O)CC(=O)N2c1cccc(F)c1]

trans-8-Benzyl-1-(3-fluorophenyl)-7-methyl-1,8-diazaspiro[4.5]decane-2,4-dione was prepared from ethyl trans-4-amino-8-benzyl-1-(3-fluorophenyl)-7-methyl-2-oxo-1,8-diazaspiro[4.5]dec-3-ene-3-carboxylate (Intermediate 1A.3-2, 1.8 g, 4.1 mmol) in a manner similar to Intermediate 1A.4-1. LCMS (M+H) 467.0.

INTERMEDIATE 1B.4-A

Benzyl trans-6-(3-fluorophenyl)-2-isopropyl-2'-methyl-5-oxo-5,6-dihydro-1'H-spiro[imidazo[1,5-a]imidazole-7,4'-piperidine]-1'-carboxylate

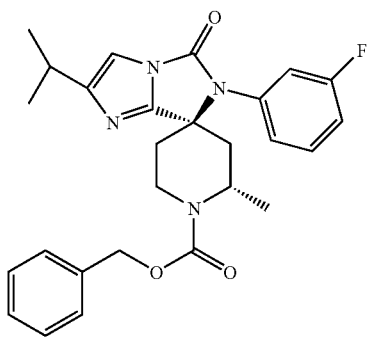 [SMILES: CC(C)c1cn2c(n1)[C@]1(CCN(C(=O)OCc3ccccc3)[C@@H](C)C1)N(c1cccc(F)c1)C2=O]

Step A: Amination with Aminoalcohol
A neat solution of benzyl trans-4-amino-1-(3-fluorophenyl)-7-methyl-2-oxo-1,3,8-triazaspiro[4.5]dec-3-ene-8-carboxylate (Intermediate 1B.3 previously described in International Patent Application WO 2007/11833, 1.0 g, 2.4 mmol) in DL-2-amino-3-methyl-1-butanol (3.8 g, 36.5 mmol) was allowed to stir at 115° C. for 18 h. Toluene (2 ml) was added to improve stirring, and the reaction was allowed to stir at 115° C. for an additional 24 h. The reaction was cooled to rt and diluted with EtOAc/hexanes. The resulting precipitate was isolated via filtration to afford benzyl trans-1-(3-fluorophenyl)-4-{[1-(hydroxymethyl)-2-methylpropyl]amino}-7-methyl-2-oxo-1,3,8-triazaspiro[4.5]dec-3-ene-8-carboxylate (83%).

Step B: Oxidation to Aldehyde
To a solution of benzyl trans-1-(3-fluorophenyl)-4-{[1-(hydroxymethyl)-2-methylpropyl]amino}-7-methyl-2-oxo-1,3,8-triazaspiro[4.5]dec-3-ene-8-carboxylate (0.90 mg, 1.8 mmol) and triethylamine (1.3 ml, 9.1 mmol) in 1:1 dichloromethane/DMSO (10 ml) at 0° C. was added dropwise a solution of sulfur trioxide-pyridine in DMSO (1.4 g, 9.1 mmol). The reaction was allowed to stir at 0° C. for 1 h. Brine was added to the reaction, and the product was extracted with EtOAc (2×). The combined organic extractions were washed with 1N sodium thiosulfate (2×) and brine, dried over sodium sulfate, filtered, and concentrated in vacuo. The crude oil was purified via flash chromatography (silica, 0-100% EtOAc/hexanes) to afford both the ring closure product benzyl trans-6-(3-fluorophenyl)-2-isopropyl-2'-methyl-5-oxo-5,6-dihydro-1'H-spiro[imidazo[1,5-a]imidazole-7,4'-piperidine]-1'-carboxylate (38%) and the aldehyde benzyl trans-1-(3-fluorophenyl)-4-[(1-formyl-2-methylpropyl)amino]-7-methyl-2-oxo-1,3,8-triazaspiro[4.5]dec-3-ene-8-carboxylate (19%).

Step C: Ring Closure
A solution of benzyl trans-1-(3-fluorophenyl)-4-[(1-formyl-2-methylpropyl)amino]-7-methyl-2-oxo-1,3,8-triazaspiro[4.5]dec-3-ene-8-carboxylate (167 mg, 0.35 mmol) in toluene with 5 A molecular sieves was allowed to stir at 70° C. for several hours with no reaction. To the reaction was added p-toluenesulfonic acid monohydrate (3.3 mg, 0.02 mmol). The reaction was allowed to stir at 50° C. for 18 h. The reaction temperature was increased to 65° C. for 8 h, decreased to 55° C. for 18 h, and then increased to 70° C. for an additional 2 h. Sat'd sodium bicarbonate was added to the reaction, and the product was extracted with dichloromethane (2×). The combined organic extractions were dried over sodium sulfate, filtered, and concentrated in vacuo to yield benzyl trans-6-(3-fluorophenyl)-2-isopropyl-2'-methyl-5-oxo-5,6-dihydro-1'H-spiro[imidazo[1,5-a]imidazole-7,4'-piperidine]-1'-carboxylate (100%). LCMS (M+H) 477.2.

INTERMEDIATE 1B.4-C

Benzyl trans-2-ethyl-6-(3-fluorophenyl)-2'-methyl-5-oxo-5,6-dihydro-1'H-spiro[imidazo[1.5-a]imidazole-7,4'-piperidine]-1'-carboxylate

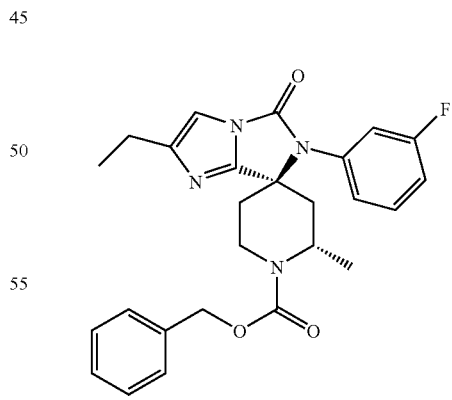

To a solution of benzyl trans-4-amino-1-(3-fluorophenyl)-7-methyl-2-oxo-1,3,8-triazaspiro[4.5]dec-3-ene-8-carboxylate (Intermediate 1B.3 previously described in International Patent Application WO 2007/11833, 100 mg, 0.24 mmol) in DMF (1.5 ml) was added 1-bromo-2-butanone (25 μl, 0.24 mmol). The reaction was allowed to stir at 90° C. for 18 h. The reaction was purified via reverse phase chromatography to yield benzyl trans-2-ethyl-6-(3-fluorophenyl)-2'-methyl-5-oxo-5,6-dihydro-1'H-spiro[imidazo[1,5-a]imidazole-7,4'-piperidine]-1'-carboxylate. LCMS (M+H) 463.2.

INTERMEDIATE 2A.1-A trans-1-Benzyl-4-(4'-bromo-4-fluoro-1,1'-biphenyl-2-yl)-2-methylpiperidine-4-carbonitrile

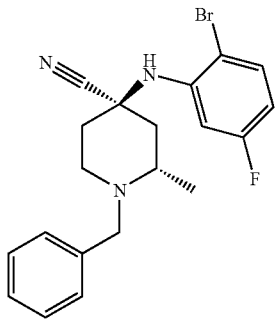 [SMILES: C[C@H]1C[C@](C#N)(Nc2cc(F)ccc2Br)CCN1Cc1ccccc1]

To a solution of 1-benzyl-2-methylpiperidin-4-one (preparation similar to that described by M.-J. Blanco-Pilado et al in International Patent Application WO2004/094380 using benzyl amine as the amine, 4.30 g, 21.2 mmol) in acetic acid (20 ml) at 0° C. were added 2-bromo-4-fluoroaniline (4.02 g, 21.2 mmol) and trimethylsilyl cyanide (2.82 ml, 21.2 mmol). The reaction was allowed to warm to rt and was then heated to 70° C. After 48 h, additional trimethylsilyl cyanide (2.82 ml, 21.2 mmol) was added to the reaction. The reaction was heated to 70° C. and allowed to stir for 7 days. The reaction was poured onto cold ammonium hydroxide and crushed ice and adjusted to pH 10. The product was extracted with dichloromethane (3×50 ml), washed with brine, dried over sodium sulfate, filtered, and concentrated in vacuo. The crude oil was purified via flash chromatography (silica, 0-20% EtOAc/hexanes) to isolate both cis- and trans-1-benzyl-4-(4'-bromo-4-fluoro-1,1'-biphenyl-2-yl)-2-methylpiperidine-4-carbonitrile (16% yield trans isomer). LCMS (M+H) 401.9. $^1$H NMR (400 MHz, CDCl$_3$) δ 7.39 (dd, J=8.8, 6.0 Hz, 1H), 7.26 (m, 5H), 6.84 (dd, J=10.8, 2.8 Hz, 1H), 6.44 (td, J=8.2, 2.4 Hz, 1H), 4.48 (s, 1H), 4.09 (d, J=14.4 Hz, 1H), 3.08 (d, J=13.6 Hz, 1H), 2.64 (m, 1H), 2.55 (m, 1H), 2.32 (dt, J=14.0, 2.8 Hz, 1H), 2.27 (dt, J=11.5, 2.9 Hz, 1H), 2.08 (m, 3H), 1.22 (d, J=6.4 Hz, 3H).

INTERMEDIATE 2A.2-A trans-1-Benzyl-4-[4-fluoro-4'-(methylsulfonyl)-1,1'-biphenyl-2-yl]-2-methylpiperidine-4-carbonitrile

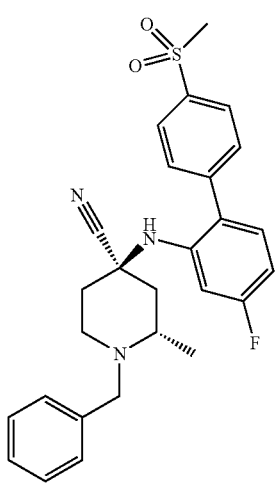 [SMILES: C[C@H]1C[C@](C#N)(Nc2cc(F)ccc2-c2ccc(S(C)(=O)=O)cc2)CCN1Cc1ccccc1]

To a solution of trans-1-benzyl-4-(4'-bromo-4-fluoro-1,1'-biphenyl-2-yl)-2-methylpiperidine-4-carbonitrile (Intermediate 2A.1-A, 100 mg, 0.25 mmol) in DMF/water (80/20 v/v, 0.6 ml) under a nitrogen atmosphere were added 4-(methanesulfonyl)phenylboronic acid (74.7 mg, 0.37 mmol), tris(4,6-dimethyl-3-sulfanatophenyl)phosphine trisodium salt hydrate (24.4 mg, 0.04 mmol), palladium(II) acetate (2.8 mg, 0.01 mmol), and diisopropyl amine (0.1 ml, 0.75 mmol). The reaction mixture was vortexed briefly to dissolve the catalyst and was stirred at 40° C. for 18 h. The reaction was purified via reverse phase chromatography to yield trans-1-benzyl-4-[4-fluoro-4'-(methylsulfonyl)-1,1'-biphenyl-2-yl]-2-methylpiperidine-4-carbonitrile. LCMS (M+H) 478.0. $^1$H NMR (400 MHz, CDCl$_3$) δ 7.96 (d, J=8.0 Hz, 2H), 7.47 (d, J=8.0 Hz, 2H), 7.32 (m, 3H), 7.25 (m, 2H), 7.04 (dd, J=8.4, 6.4 Hz, 1H), 6.85 (dd, J=11.2, 2.4 Hz, 1H), 6.62 (td, J=8.2, 2.3 Hz, 1H), 3.97 (d, J=13.6 Hz, 1H), 3.68 (s, 1H), 3.23 (d, J=13.2 Hz, 1H), 3.11 (s, 3H), 2.62 (dt, J=12.3, 3.1 Hz, 1H), 2.24 (m, 3H), 2.10 (dt, J=12.9, 3.7 Hz, 1H), 1.99 (m, 2H), 1.20 (d, J=5.6 Hz, 3H).

INTERMEDIATE 2A.1-B 4-fluoro-4'-(methylsulfonyl)-1,1'-biphenyl-2-amine

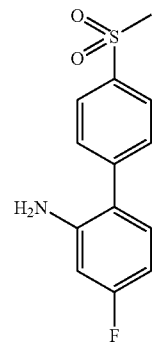 [SMILES: CS(=O)(=O)c1ccc(-c2ccc(F)cc2N)cc1]

To a solution of 2-bromo-4-fluoroaniline (5.0 g, 26.3 mmol) in DMF/water (80/20 v/v, 65.8 ml) under an atmosphere of nitrogen were added 4-(methanesulfonyl)phenylboronic acid (7.9 g, 39.5 mmol), tris(4,6-dimethyl-3-sulfanatophenyl)phosphine trisodium salt hydrate (2.6 g, 4.0 mmol), palladium(II) acetate (0.3 g, 1.3 mmol), and diisopropyl amine (11.3 ml, 79.0 mmol). The reaction was allowed to stir at 50° C. for 2.5 h. The reaction was diluted with EtOAc and washed with 3M LiCl (3×), water, and brine. The organic portion was dried over sodium sulfate, filtered, and concentrated in vacuo to afford 4-fluoro-4'-(methylsulfonyl)-1,1'-biphenyl-2-amine as a yellow solid (95%). LCMS (M+H) 266.1. $^1$H NMR (400 MHz, CD$_3$OD) δ 8.02 (m, 2H), 7.65 (m, 2H), 7.05 (dd, J=8.6, 6.2 Hz, 1H), 6.57-6.47 (m, 2H), 3.86 (s, 2H), 3.11 (s, 3H).

INTERMEDIATE 2A.2-B trans-1-Benzyl-4-[4-fluoro-4'-(methylsulfonyl)-1,1'-biphenyl-2-yl]-2-methylpiperidine-4-carbonitrile

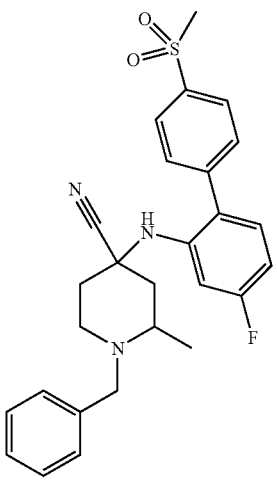 [SMILES: CC1CC(C#N)(Nc2cc(F)ccc2-c2ccc(S(C)(=O)=O)cc2)CCN1Cc1ccccc1]

To a solution of 1-benzyl-2-methylpiperidin-4-one (preparation similar to that described by M.-J. Blanco-Pilado et al in International Patent Application WO2004/094380 using benzyl amine as the amine, 625 mg, 3.1 mmol) and 4-fluoro-4'-(methylsulfonyl)-1,1'-biphenyl-2-amine (Intermediate 2A.1-B, 1.14 g, 4.3 mmol) in 1,2-dichloroethane (15.4 ml) at 0° C. was added titanium tetrachloride (0.2 ml in 0.1 ml 1,2-dichloroethane) dropwise. The reaction was allowed to warm to rt and stir for 10 min and was then heated to 60° C. After 5 min, trimethylsilyl cyanide (0.5 ml, 3.7 mmol) was added to the reaction mixture. The reaction continued to stir at 60° C. for 1.5 h and was then quenched by pouring onto aq ammonium hydroxide and ice. The product was extracted with EtOAc, and the extractions were washed with sat'd sodium bicarbonate and brine, dried over sodium sulfate, filtered, and concentrated in vacuo. The crude material was purified via flash chromatography (silica, 0-70% EtOAc/hexanes) to obtain trans-1-benzyl-4-[4-fluoro-4'-(methylsulfonyl)-1,1'-biphenyl-2-yl]-2-methylpiperidine-4-carbonitrile (13%). LCMS (M+H) 478.0. $^1$H NMR (400 MHz, CD$_3$OD) δ 7.90 (dd, J=6.6, 1.8 Hz, 2H), 7.49 (dd, J=6.6, 1.8 Hz, 2H), 7.40-7.30 (m, 5H), 7.13 (dd, J=8.4, 6.4 Hz, 1H), 6.90 (dd, J=12.0, 2.4 Hz, 1H), 6.67 (td, J=8.3, 1.9 Hz, 1H), 4.65 (s, 1H), 3.96 (d, J=13.6 Hz, 1H), 3.49 (d, J=13.6 Hz, 1H), 3.16 (s, 3H), 2.64 (dt, J=12.3, 3.1 Hz, 1H), 2.41 (m, 3H), 2.20 (td, J=12.5, 1.9 Hz, 1H), 1.87 (dd, J=14.0, 11.6 Hz, 1H), 1.24 (m, 3H).

EXAMPLE 1

1-Benzyl-6'-(3-fluorophenyl)-1',2',3',4'-tetrahydrospiro[piperidine-4,7'-pyrrolo[3,4-b]pyridin]-5'(6'H)-one

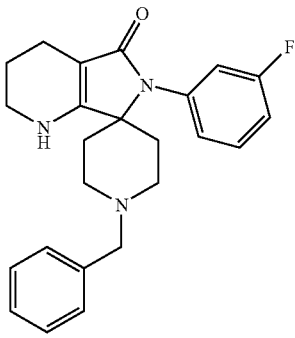 [SMILES: O=C1C2=C(NCCC2)C2(CCN(Cc3ccccc3)CC2)N1c1cccc(F)c1]

To a solution of 8-benzyl-1-(3-fluorophenyl)-1,8-diazaspiro[4.5]decane-2,4-dione (Intermediate 1A.4-1, 300 mg, 0.85 mmol) in isopropanol (4.3 ml) were added 3-bromopropylamine hydrobromide (205 mg, 0.94 mmol) and 2,6-lutidine (0.22 ml, 1.87 mmol). The reaction vessel was sealed and heated at 80° C. for 3 days. The reaction was concentrated in vacuo and partitioned between dichloromethane and 1N NaOH. The organic layer was washed with brine, dried over sodium sulfate, filtered, and concentrated in vacuo. The crude material was purified via flash chromatography (silica, 0-5% methanol (10% NH$_4$OH)/dichloromethane) to yield 1-benzyl-6'-(3-fluorophenyl)-1',2',3',4'-tetrahydrospiro[piperidine-4,7'-pyrrolo[3,4-b]pyridin]-5'(6'H)-one. LCMS (M+H) 392.1. $^1$H NMR (400 MHz, CDCl$_3$) δ 7.28 (m, 6H), 7.03 (td, J=8.2, 2.0 Hz, 1H), 6.97 (d, J=7.9 Hz, 1H), 6.92 (dt, J=9.9, 2.1 Hz, 1H), 3.46 (s, 2H), 3.33 (m, 2H), 2.52 (t, J=6.1 Hz, 41H), 2.33 (t, J=6.2 Hz, 2H), 2.06 (quint, J=6.9 Hz, 2H), 1.84 (m, 4H).

EXAMPLE 2 trans-5R,7S-1-Benzyl-6'-(3-fluorophenyl)-2-methyl-1',2',3',4'-tetrahydrospiro[piperidine-4,7'-pyrrolo[3,4-b]pyridin]-5'(6'H)-one

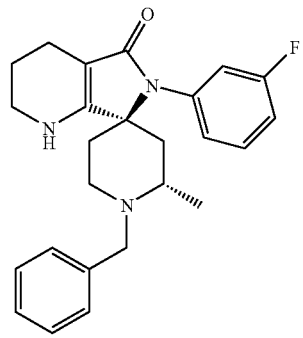 [SMILES: C[C@H]1C[C@]2(CCN1Cc1ccccc1)C1=C(CCCN1)C(=O)N2c1cccc(F)c1]

Step A: Amine Condensation

To a solution of trans-8-benzyl-1-(3-fluorophenyl)-7-methyl-1,8-diazaspiro[4.5]decane-2,4-dione (Intermediate 1A.4-2, 300 mg, 0.82 mmol) in absolute ethanol (2.75 ml) with molecular sieves under an atmosphere of nitrogen was added 3-chloropropylamine hydrochloride (138 mg, 1.1 mmol). The reaction was vortexed briefly and allowed to stir at 115° C. for 20 min. The reaction temperature was decreased to 80° C. and stirred for 18 h. The reaction was cooled to rt, and 2,6-lutidine (238 dl, 2.0 mmol) was added to affect ring closure. The reaction was allowed to stir at rt for 8 h, but no reaction occurred. The reaction was poured onto aq sodium bicarbonate, and the product was extracted with EtOAc (3×). The combined organic extractions were dried over sodium sulfate, filtered, and concentrated in vacuo. The crude product was purified via flash chromatography (silica, 0-100% EtOAc/hexanes) and recrystallized from EtOAc to afford trans-8-benzyl-4-[(3-chloropropyl)amino]-1-(3-fluorophenyl)-7-methyl-1,8-diazaspiro[4.5]dec-3-en-2-one (19%). LCMS (M+H) 442.1.

Step B: Ring Closure

To a solution of trans-8-benzyl-4-[(3-chloropropyl)amino]-1-(3-fluorophenyl)-7-methyl-1,8-diazaspiro[4.5]dec-3-en-2-one (65 mg, 0.15 mmol) in acetone were added potassium iodide (73 mg, 0.44 mmol) and potassium carbonate (41 mg, 0.29 mmol). The reaction was allowed to stir at 65° C. for 2 days and then heated to 75° C. in a microwave reactor for 20 min to drive the reaction to completion. The reaction was diluted with water and the product was extracted with dichloromethane (2×). The combined organic extractions were dried over sodium sulfate, filtered, and concentrated in vacuo. The crude material was purified via reverse phase chromatography to yield trans-5R,7S-1-benzyl-6'-(3-fluorophenyl)-2-methyl-1',2',3',4'-tetrahydrospiro[piperidine-4,7'-pyrrolo[3,4-b]pyridin]-5'(6'H)-one. LCMS (M+H) 406.1. $^1$H NMR (400 MHz, CD$_3$OD) δ 7.48 (t, J=8.5 Hz, 1.5H), 7.38 (t, J=8.5 Hz, 1.5H), 7.21 (m, 3H), 6.97 (m, 3H), 4.29 (s, 2H), 3.37 (s, 2H), 2.90 (m, 1H), 2.46 (m, 2H), 2.33 (d, J=7.6 Hz, 3H), 2.20 (m, 3H), 1.81 (m, 2H), 1.53 (d, J=5.6 Hz, 3H).

EXAMPLE 3

1-Benzyl-5'-(3-fluorophenyl)-1'H-spiro[piperidine-4,6'-pyrrolo[3,4-b]pyrrol]-4'(5'H)-one

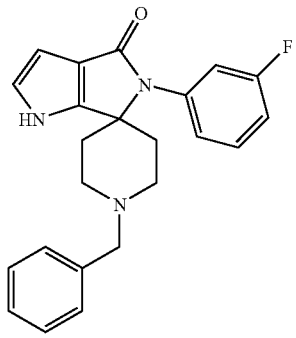 [SMILES: O=C1c2cc[nH]c2C2(CCN(Cc3ccccc3)CC2)N1c1cccc(F)c1]

To a solution of 8-benzyl-1-(3-fluorophenyl)-1,8-diazaspiro[4.5]decane-2,4-dione (Intermediate 1A.4-1, 100 mg, 0.29 mmol) in methanol (0.1 ml) was added 2,2-dimethoxyethylamine (2 ml). The reaction was allowed to stir at 100° C. until the starting material was consumed. The reaction was concentrated in vacuo, and the residue was dissolved in toluene. The reaction was treated with a catalytic amount of p-toluenesulfonic acid and allowed to stir at 110° C. for 18 h. The crude reaction was purified via reverse phase chromatography to yield 1-benzyl-5'-(3-fluorophenyl)-1'H-spiro[piperidine-4,6'-pyrrolo[3,4-b]pyrrol]-4'(5'H)-one. LCMS (M+H) 376.1. $^1$H NMR (400 MHz, CD$_3$OD) δ 7.50 (m, 7H), 7.23 (td, J=8.4, 2.1 Hz, 2H), 7.07 (m, 3H), 6.43 (d, J=2.8 Hz, 1H), 4.41 (s, 2H), 3.64 (d, J=13.6 Hz, 2H), 3.43 (t, J=12.6 Hz, 3H), 2.28 (td, J=14.1, 4.0 Hz, 2H), 2.02 (d, J=15.6 Hz, 2H).

EXAMPLE 4 trans-5R,7S-6-(3-fluorophenyl)-1'-(3-isopropoxybenzyl)-2-isopropyl-2'-methylspiro[imidazo[1,5-a]imidazole-7,4'-piperidin]-5(6H)-one

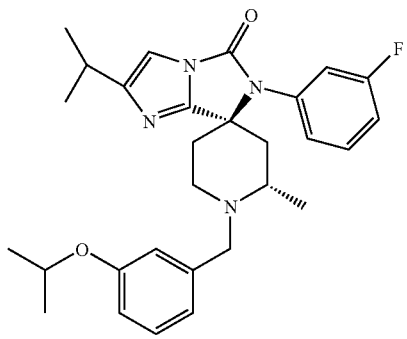 [SMILES: CC(C)Oc1cccc(CN2CC[C@@]3(C[C@@H]2C)c2nc(C(C)C)cn2C(=O)N3c2cccc(F)c2)c1]

Deprotection Step: To a solution of benzyl trans-6-(3-fluorophenyl)-2-isopropyl-2'-methyl-5-oxo-5,6-dihydro-1'H-spiro[imidazo[1,5-a]imidazole-7,4'-piperidine]-1'-carboxylate (Intermediate 1B.4-A, 485 mg, 1.02 mmol) in ethanol was added palladium hydroxide. The reaction was charged with hydrogen gas (1 atm) and allowed to stir at 50° C. for 30 min. The reaction mixture was filtered through Celite, and the filtrate was concentrated in vacuo to yield trans-6-(3-fluorophenyl)-2-isopropyl-2'-methylspiro[imidazo[1,5-a]imidazole-7,4'-piperidin]5(6H)-one (99%). LCMS (M+H) 343.1

Alkylatio Step: A flask charged with trans-6-(3-fluorophenyl)-2-isopropyl-2'-methylspiro[imidazo[1,5-a]imidazole-7,4'-piperidin]5(6H)-one (60 mg, 0.18 mmol), potassium carbonate (121 mg, 0.88 mmol), and sodium iodide (1.3 mg, 0.0088 mmol) in DMSO (1 ml) was heated to 65° C. 1-(chloromethyl)-3-isopropoxybenzene (31 mg, 0.17 mmol) was added to the reaction, and the solution was allowed to stir at 65° C. for 18 h. The reaction was purified via reverse phase chromatography to yield trans-5R,7S-6-(3-fluorophenyl)-1'-(3-isopropoxybenzyl)-2-isopropyl-2'-methylspiro[imidazo[1,5-a]imidazole-7,4'-piperidin]-5(6H)-one. LCMS (M+H) 491.1. $^1$H NMR (400 MHz, CD$_3$OD) δ 7.55 (s, 0.5H), 7.32-7.15 (m, 5.5H), 7.02 (s, 2.5H), 6.75 (s, 1.5H), 4.61 (sept, J=6.0 Hz, 1H), 4.33 (m, 2H), 3.82 (m, 1H), 3.51 (s, 0.5H), 2.94 (quint, J=6.8 Hz, 2H), 2.72-2.29 (m, 5H), 1.82 (s, 1.5H), 1.59 (s, 1.5H), 1.29 (d, J=6.8 Hz, 12H).

EXAMPLE 5

1'-Benzyl-6-[4-fluoro-4'-(methylsulfonyl)biphenyl-2-yl]-2'-methylspiro[imidazo[1,5-a]imidazole-7,4'-piperidin]-5(6H)-one

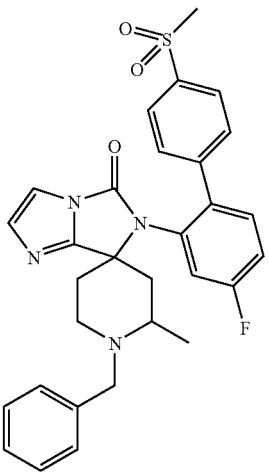 [SMILES: CC1CC2(CCN1Cc1ccccc1)c1nccn1C(=O)N2c1cc(F)ccc1-c1ccc(S(C)(=O)=O)cc1]

Step A: Formation of Iminohydantoin

To a solution of 1-benzyl-4-[4-fluoro-4'-(methylsulfonyl)-1,1'-biphenyl-2-yl]-2-methylpiperidine-4-carbonitrile (Intermediate 2A.2-B, 200 mg, 0.42 mmol) in 1,2-dichloroethane (4 ml) at 0° C. under an atmosphere of nitrogen was added chlorosulfonyl isocyanate (37 μl, 0.42 mmol) dropwise. The reaction was warmed to rt and allowed to stir for 8 h. The reaction was again cooled to 0° C. and additional chlorosulfonyl isocyanate (37 μl, 0.42 mmol) was added dropwise. The reaction was warmed to rt and allowed to stir for 18 h. To the reaction was added methanol (100 μl), water (40 μl), and diisopropylethylamine (75 μl, 0.42 mmol). The reaction was allowed to stir at 65° C. for 2 h and was then concentrated in vacuo. The residue was dissolved in EtOAc and washed with water and brine. The organic portion was dried over sodium sulfate, filtered, concentrated in vacuo, and purified via reverse phase chromatography to yield 4-amino-8-benzyl-1-[4-fluoro-4'-(methylsulfonyl)biphenyl-2-yl]-7-methyl-1,3,8-triazaspiro[4.5]dec-3-en-2-one. LCMS (M+H) 521.0.

Step B: Amination

A solution of 4-amino-8-benzyl-1-[4-fluoro-4'-(methylsulfonyl)biphenyl-2-yl]-7-methyl-1,3,8-triazaspiro[4.5]dec-3-en-2-one (50 mg, 0.10 mmol) in 2,2-dimethoxyethylamine (2.0 ml) was sealed and allowed to stir at 85° C. for 18 h. The temperature was increased to 110° C., and the reaction was allowed to stir for an additional 16 h. The reaction was diluted with EtOAc and washed with brine. The organic portion was dried over sodium sulfate, filtered, and concentrated in vacuo to yield 8-benzyl-4-[(2,2-dimethoxyethyl)amino]-1-[4-fluoro-4'-(methylsulfonyl)biphenyl-2-yl]-7-methyl-1,3,8-triazaspiro[4.5]dec-3-en-2-one. LCMS (M+H) 609.0.

Step C: Ring Closure

To a solution of 8-benzyl-4-[(2,2-dimethoxyethyl)amino]-1-[4-fluoro-4'-(methylsulfonyl)biphenyl-2-yl]-7-methyl-1,3,8-triazaspiro[4.5]dec-3-en-2-one (50 mg, 0.08 mmol) in toluene (2.0 ml) was added p-toluenesulfonic acid (20 mg, 0.01 mmol). The reaction was sealed and allowed to stir at 110° C. The reaction was purified via reverse phase chromatography and neutralized with sodium bicarbonate. The product was extracted with EtOAc, dried over sodium sulfate, filtered, and concentrated in vacuo to yield the title compound as cis and trans mixture-1'-benzyl-6-[4-fluoro-4'-(methylsulfonyl)biphenyl-2-yl]-2'-methylspiro[imidazo[1,5-a]imidazole-7,4'-piperidin]-5(6H)-one. LCMS (M+H) 544.9. $^1$H NMR (400 MHz, CD$_3$OD) δ 7.98 (m, 1H), 7.89 (m, 1H), 7.66 (m, 3H), 7.55 (m, 1H), 7.46 (m, 1H), 7.40 (dt, J=8.8, 2.8 Hz, 0.5H), 7.32 (dt, J=9.2, 2.8 Hz, 0.5H), 7.22 (m, 5H), 6.91 (m, 0.5H), 6.79 (m, 0.5H), 4.10 (m, 1H), 3.12 (s, 1.5H), 3.06 (s, 1.5H), 3.02 (s, 1H), 2.81 (m, 1H), 2.71-2.40 (m, 2H), 2.04-1.85 (m, 1H), 1.78-1.57 (m, 3H), 1.32 (s, 3H).

The following examples in Table 1 were prepared using one of the preceding methods with the referenced intermediates.

TABLE 1

The following additional compounds of the invention were synthesized.

| EX | Intermediate | Structure | MS M+H | IUPAC NAME |
|---|---|---|---|---|
| 6 | IB.4-A | 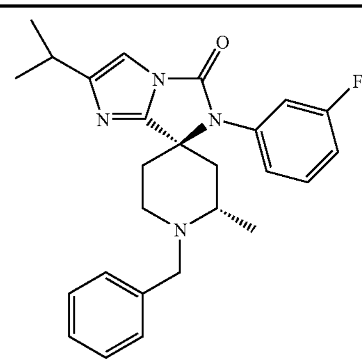 | 433 | trans-(5R,7S)-1'-benzyl-6-(3-fluorophenyl)-2-isopropyl-2'-methylspiro[imidazo[1,5-a]imidazole-7,4'-piperidin]-5(6H)-one |
| 7 | IB.4-B | 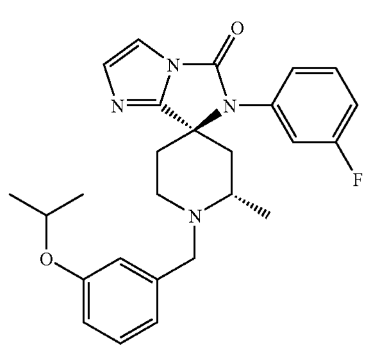 [SMILES: CC(C)Oc1cccc(CN2CC[C@@]3(C[C@@H]2C)c2nccn2C(=O)N3c2cccc(F)c2)c1] | 449 | trans-(5R,7S)-6-(3-fluorophenyl)-1'-(3-isopropoxybenzyl)-2'-methylspiro[imidazo[1,5-a]imidazole-7,4'-piperidin]-5(6H)-one |

TABLE 1-continued

The following additional compounds of the invention were synthesized.

| EX | Intermediate | Structure | MS M + H | IUPAC NAME |
|---|---|---|---|---|
| 8 | IB.4-C | 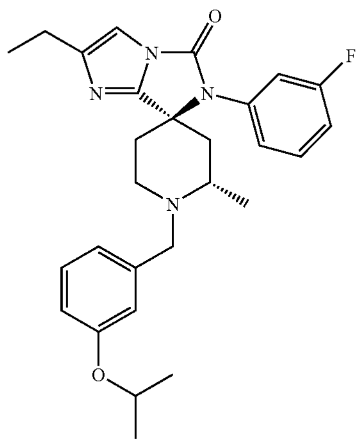 [SMILES: CCc1cn2c(n1)[C@]1(CCN(Cc3cccc(OC(C)C)c3)[C@@H](C)C1)N(c1cccc(F)c1)C2=O] | 477 | trans-(5R,7S)-2-ethyl-6-(3-fluorophenyl)-1'-(3-isopropoxybenzyl)-2'-methylspiro[imidazo[1,5-a]imidazole-7,4'-piperidin]-5(6H)-one |
| 9 | IB.4-C | 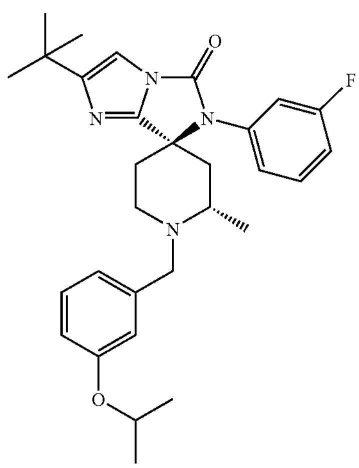 [SMILES: CC(C)Oc1cccc(CN2CC[C@@]3(C[C@@H]2C)c2nc(C(C)(C)C)cn2C(=O)N3c2cccc(F)c2)c1] | 505 | trans-(5R,7S)-2-tert-butyl-6-(3-fluorophenyl)-1'-(3-isopropoxybenzyl)-2'-methylspiro[imidazo[1,5-a]imidazole-7,4'-piperidin]-5(6H)-one |
| 10 | 2A.1-B | 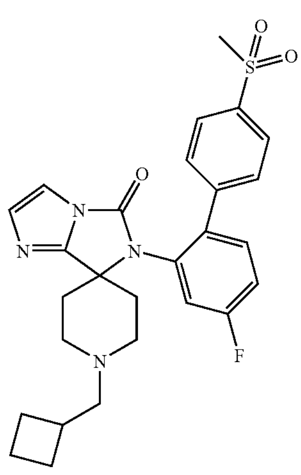 [SMILES: CS(=O)(=O)c1ccc(-c2ccc(F)cc2N2C(=O)n3ccnc3C23CCN(CC2CCC2)CC3)cc1] | 509 | 1'-(cyclobutylmethyl)-6-[4-fluoro-4'-(methylsulfonyl)biphenyl-2-yl]spiro[imidazo[1,5-a]imidazole-7,4'-piperidin]-5(6H)-one |

Compounds in Table 1 having a basic group or acidic group are depicted and named as the free base. Depending on the reaction and purification conditions, various compounds in Table 1 having a basic group were isolated in either the free base form, or as a salt (such as HCl salt), or in both free base and salt forms.

The following abbreviations are used throughout the text:

| | |
|---|---|
| Me: | methyl |
| Et: | ethyl |
| Bu: | butyl |
| t-Bu: | tert-butyl |
| i-Bu: | iso-butyl |
| Pr: | propyl |
| i-Pr: | iso-propyl |
| Ar: | aryl |
| Ph: | phenyl |
| Bn: | benzyl |
| TMS: | trimethyl silyl |
| DMSO: | dimethylsulfoxide |
| DMF: | N,N'-dimethylformamide |
| DIPEA: | diisopropyl ethyl amine |
| Ts: | tosyl |
| Ac: | acetyl |
| aq: | aqueous |
| rt | room temperature |
| h: | hours |
| min: | minutes |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (IA):

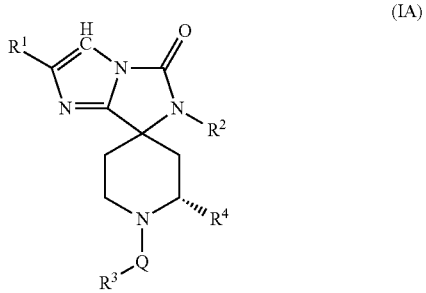

(IA)

wherein:
$R^1$ is selected from the group consisting of
(1) hydrogen, and
(2) —$C_{1-10}$ alkyl;
$R^2$ is phenyl, wherein said phenyl $R^2$ moiety is optionally substituted with one or more moieties selected from the group consisting of:
(a) halo,
(b) —OH,
(c) —CN,
(d) —$C_{1-10}$ alkyl,
(e) —$C_{3-12}$ cycloalkyl,
(f) —O—$C_{1-10}$ alkyl,
(g) —$C_{0-6}$ alkyl-aryl, and
(h) —$C_{0-6}$ alkyl-heteroaryl,
  wherein said alkyl, cycloalkyl, aryl, and heteroaryl moiety is optionally substituted with one or more
  (i) halo,
  (ii) -OH,
  (iii) —CN,
  (iv) —$C_{1-6}$ alkyl, wherein said alkyl is optionally substituted with one or more halo,
  (v) —$OC_{1-6}$ alkyl,
  (vi) —$C_{2-6}$ alkenyl, or
  (vii) —$SO_2C_{1-3}$ alkyl;
Q is —$CH_2$—;
$R^3$ is phenyl, wherein said phenyl $R^3$ moiety is optionally substituted with one or more moieties selected from the group consisting of:
(a) halo,
(b) —OH,
(c) —CN,
(d) —$C_{1-10}$ alkyl,
(e) —$C_{2-10}$ alkenyl,
(f) —$C_{3-12}$ cycloalkyl,
(g) —C—$C_{3-12}$ cycloalkyl, and
(h) —O—$C_{1-10}$ alkyl,
  wherein said alkyl, alkenyl, and cycloalkyl, moiety is optionally substituted with one or more
  (i) halo,
  (ii) -OH,
  (iii) —CN,
  (iv) —$C_{1-6}$ alkyl, wherein said alkyl is optionally substituted with one or more halo,
  (v) —$OC_{1-6}$ alkyl,
  (vi) —$C_{2-6}$ alkenyl, or
  (vii) —$SO_2C_{1-3}$ alkyl;
$R^4$ is selected from the group consisting of hydrogen and —$C_{1-0}$ alkyl;
or a pharmaceutically acceptable salt thereof.

2. A compound of claim 1, wherein $R^1$ is selected from the group consisting of hydrogen and $C_{1-4}$ alkyl.

3. A compound of claim 2, wherein $R^1$ is selected from the group consisting of H, methyl, ethyl, n-propyl, and isopropyl.

4. A compound of claim 1 which is selected from the group consisting of

| EX | Structure |
|---|---|
| 4 | 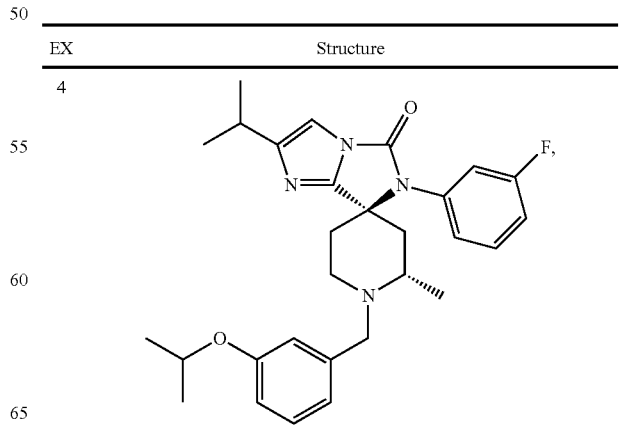 |

| EX | Structure |
|---|---|
| 5 | 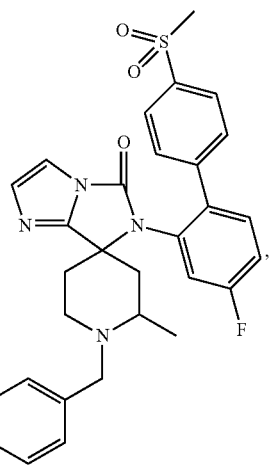 |
| 6 | 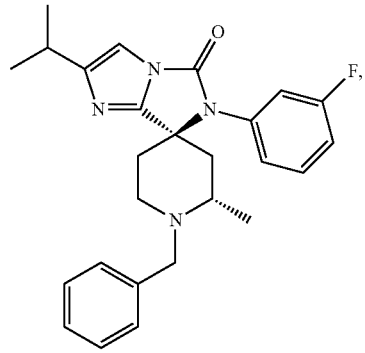 [SMILES: CC(C)c1cn2c(n1)[C@]1(CCN(Cc3ccccc3)[C@@H](C)C1)N(c1cccc(F)c1)C2=O] |
| 7 | 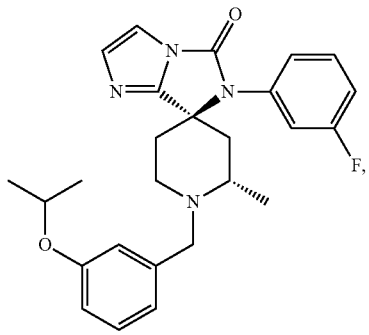 [SMILES: CC(C)Oc1cccc(CN2CC[C@@]3(C[C@@H]2C)c2nccn2C(=O)N3c2cccc(F)c2)c1] |

| EX | Structure |
|---|---|
| 8 | 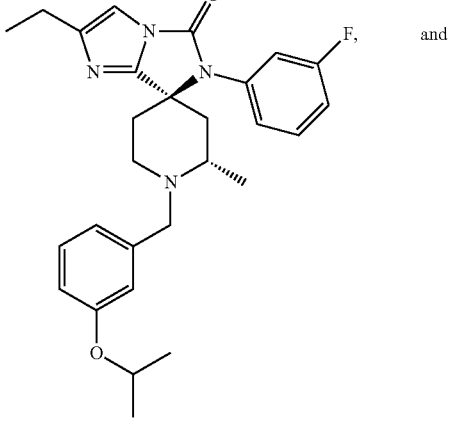 and |
| 9 | 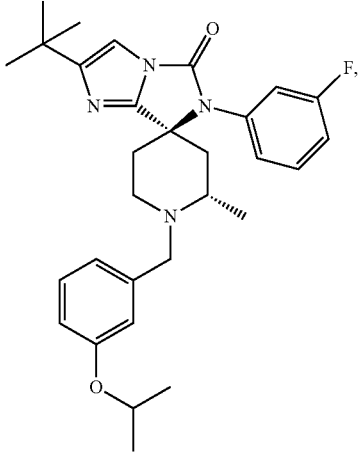 [SMILES: CC(C)Oc1cccc(CN2CC[C@@]3(C[C@@H]2C)c2nc(C(C)(C)C)cn2C(=O)N3c2cccc(F)c2)c1] | or a pharmaceutically acceptable salt thereof.

5. A pharmaceutical composition comprising a compound of claim 1, or a pharmaceutically acceptable salt thereof, and a pharmaceutically acceptable carrier.

6. A pharmaceutical composition comprising a compound of claim 1, or a pharmaceutically acceptable salt thereof, and a pharmaceutically acceptable carrier.

* * * * *